US009849127B2

(12) United States Patent
Heuser et al.

(10) Patent No.: US 9,849,127 B2
(45) Date of Patent: Dec. 26, 2017

(54) MEANS AND METHODS FOR TREATING CANCER

(71) Applicant: Medizinische Hochschule Hannover, Hannover (DE)

(72) Inventors: Michael Heuser, Hannover (DE); Anuhar Chaturvedi, Hannover (DE); Matthias Preller, Hannover (DE)

(73) Assignee: Medizinisch Hochschule Hannover, Hannover (DE)

( * ) Notice: Subject to any disclaimer, the term of this patent is extended or adjusted under 35 U.S.C. 154(b) by 0 days.

(21) Appl. No.: 14/890,959

(22) PCT Filed: May 14, 2014

(86) PCT No.: PCT/EP2014/059898
§ 371 (c)(1),
(2) Date: Nov. 13, 2015

(87) PCT Pub. No.: WO2014/184272
PCT Pub. Date: Nov. 20, 2014

(65) Prior Publication Data
US 2016/0074391 A1 Mar. 17, 2016

(30) Foreign Application Priority Data
May 14, 2013 (EP) .................................... 13167672

(51) Int. Cl.
*A61K 31/496* (2006.01)
*A01K 67/027* (2006.01)

(52) U.S. Cl.
CPC ........ *A61K 31/496* (2013.01); *A01K 67/0271* (2013.01); *A01K 67/0275* (2013.01); *A01K 2207/12* (2013.01); *A01K 2217/052* (2013.01); *A01K 2227/105* (2013.01); *A01K 2267/0331* (2013.01)

(58) Field of Classification Search
CPC .......................... A61K 31/496; A61K 2800/78
See application file for complete search history.

(56) References Cited

U.S. PATENT DOCUMENTS

| 5,068,246 | A | * | 11/1991 | Zipplies | A01N 43/36 |
| | | | | | 514/409 |
| 7,910,561 | B2 | * | 3/2011 | Arruda | C07D 471/04 |
| | | | | | 514/210.21 |
| 2011/0053943 | A1 | | 3/2011 | Claremon et al. | |
| 2012/0094992 | A1 | | 4/2012 | Brown et al. | |
| 2012/0225866 | A1 | | 9/2012 | Oshima et al. | |
| 2012/0295899 | A1 | * | 11/2012 | Mangion | C07D 498/04 |
| | | | | | 514/230.2 |
| 2012/0295903 | A1 | | 11/2012 | Blount et al. | |

FOREIGN PATENT DOCUMENTS

| WO | WO 2011/050210 | * | 4/2011 |
| WO | WO 2012/009678 | * | 1/2012 |

OTHER PUBLICATIONS

PubChem Substance. Substance ID 116304520/Chemical ID 45252004; XP002714236, Mar. 29, 2011.*
ChemBridge Corporation (compound 1070690-06-0; 2-[2-[3-(4-Fluorophenyl)-1-pyrrolidinyl]ethyl]-1,4-dimethylpiperazine; Nov. 4, 2008.*
Inglese et al, PNAS 103(31):11473-11478, 2006.*
Beatriz Alonso et al., "Using Heteroaryl-lithium Reagents as Hydroxycarbonyl Anion Equivalents in Conjugate Addition Reactions with (S, S)-(+)-Pseudoephedrine as Chiral Auxiliary; Enantioselective Synthesis of 3-Substituted Pyrrolidines" The Journal of Organic Chemistry, vol. 78. No. 2. Jan. 18, 2013, pp. 614-627.
Caio C. Oliveira et al., "Intermolecular Enantioselective Heck-Matsuda Arylations of Acyclic Olefins: Application to the Synthesis of [beta]-Aryl-[gamma]-lactones and [beta]-Aryl Aldehydes", The Journal of Organic Chemistry, vol. 78, No. 9, May 3, 2013, pp. 4373-4385.
Chaturvedi Anuhar et al. "Mutated IDH1 Has 2-Hydroxyglutarate-Independent Functions in Leukemogenesis", Blood (ASH Annual Meeting Abstracts), vol. 120, No. 21, ABS. 770, Nov. 2012, XP002714234, & 54th Annual Meeting and Exposition of the American-Society-of-Hematology (ASH); Atlanta, GA, USA; Dec. 8 -11, 2012.
D. Rohle et al., "An Inhibitor of Mutant IDH1 Delays Growth and Promotes Differentiation of Glioma Cells", Science, vol. 340, No. 6132, May 3, 2013, pp. 626-630.
Database PubChem Substance, Mar. 29, 2011, XP002714236. retrieved from NCBI Database accession No. SID 116304520.
Ducray Francois et al., "Predictive and prognostic factors for gliomas." Medscape Expert Review of Anticancer Therapy, vol. 11, No. 5 May 2011, pp. 1-12.
F. Wang et al., "Targeted Inhibition of Mutant IDH2 in Leukemia Cells Induces Cellular Differentiation", Science, vol. 340, No. 6132, May 3, 2013, pp. 622-626.
J. Kim et al., "Silencing a Metabolic Oncogene", Science, vol. 340, No. 6132, May 3, 2013, pp. 558-559.

* cited by examiner

*Primary Examiner* — Kevin Hill
(74) *Attorney, Agent, or Firm* — Foley Hoag LLP

(57) ABSTRACT

The present invention relates to a pharmaceutical composition comprising a compound of formula (I)

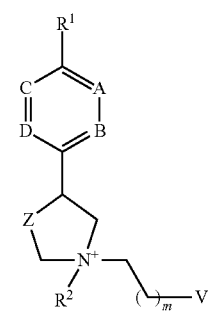

Figure 1:
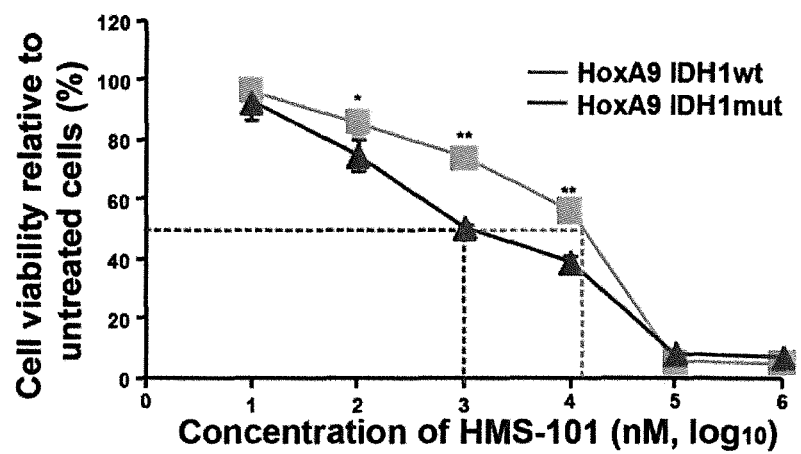

and methods of treating or preventing cell proliferation disorders comprising administering to a subject a therapeutically active amount or a preventive amount of such a compound.

5 Claims, 4 Drawing Sheets

SEQUENCE LISTING

<160> NUMBER OF SEQ ID NOS: 2

<210> SEQ ID NO 1
<211> LENGTH: 414
<212> TYPE: PRT
<213> ORGANISM: Homo sapiens
<220> FEATURE:
<223> OTHER INFORMATION: isocitrate dehydrogenase 1

<400> SEQUENCE: 1

Met Ser Lys Lys Ile Ser Gly Gly Ser Val Val Glu Met Gln Gly Asp
1               5                   10                  15

Glu Met Thr Arg Ile Ile Trp Glu Leu Ile Lys Glu Lys Leu Ile Phe
            20                  25                  30

Pro Tyr Val Glu Leu Asp Leu His Ser Tyr Asp Leu Gly Ile Glu Asn
        35                  40                  45

```
Arg Asp Ala Thr Asn Asp Gln Val Thr Lys Asp Ala Glu Ala Ile
    50                  55                  60

Lys Lys His Asn Val Gly Val Lys Cys Ala Thr Ile Thr Pro Asp Glu
65                  70                  75                  80

Lys Arg Val Glu Glu Phe Lys Leu Lys Gln Met Trp Lys Ser Pro Asn
                85                  90                  95

Gly Thr Ile Arg Asn Ile Leu Gly Gly Thr Val Phe Arg Glu Ala Ile
            100                 105                 110

Ile Cys Lys Asn Ile Pro Arg Leu Val Ser Gly Trp Val Lys Pro Ile
        115                 120                 125

Ile Ile Gly Arg His Ala Tyr Gly Asp Gln Tyr Arg Ala Thr Asp Phe
    130                 135                 140

Val Val Pro Gly Pro Gly Lys Val Glu Ile Thr Tyr Thr Pro Ser Asp
145                 150                 155                 160

Gly Thr Gln Lys Val Thr Tyr Leu Val His Asn Phe Glu Glu Gly Gly
                165                 170                 175

Gly Val Ala Met Gly Met Tyr Asn Gln Asp Lys Ser Ile Glu Asp Phe
            180                 185                 190

Ala His Ser Ser Phe Gln Met Ala Leu Ser Lys Gly Trp Pro Leu Tyr
        195                 200                 205

Leu Ser Thr Lys Asn Thr Ile Leu Lys Lys Tyr Asp Gly Arg Phe Lys
    210                 215                 220

Asp Ile Phe Gln Glu Ile Tyr Asp Lys Gln Tyr Lys Ser Gln Phe Glu
225                 230                 235                 240

Ala Gln Lys Ile Trp Tyr Glu His Arg Leu Ile Asp Asp Met Val Ala
                245                 250                 255

Gln Ala Met Lys Ser Glu Gly Gly Phe Ile Trp Ala Cys Lys Asn Tyr
            260                 265                 270

Asp Gly Asp Val Gln Ser Asp Ser Val Ala Gln Gly Tyr Gly Ser Leu
        275                 280                 285

Gly Met Met Thr Ser Val Leu Val Cys Pro Asp Gly Lys Thr Val Glu
    290                 295                 300

Ala Glu Ala Ala His Gly Thr Val Thr Arg His Tyr Arg Met Tyr Gln
305                 310                 315                 320

Lys Gly Gln Glu Thr Ser Thr Asn Pro Ile Ala Ser Ile Phe Ala Trp
                325                 330                 335

Thr Arg Gly Leu Ala His Arg Ala Lys Leu Asp Asn Asn Lys Glu Leu
            340                 345                 350

Ala Phe Phe Ala Asn Ala Leu Glu Glu Val Ser Ile Glu Thr Ile Glu
        355                 360                 365

Ala Gly Phe Met Thr Lys Asp Leu Ala Ala Cys Ile Lys Gly Leu Pro
    370                 375                 380

Asn Val Gln Arg Ser Asp Tyr Leu Asn Thr Phe Glu Phe Met Asp Lys
385                 390                 395                 400

Leu Gly Glu Asn Leu Lys Ile Lys Leu Ala Gln Ala Lys Leu
                405                 410

<210> SEQ ID NO 2
<211> LENGTH: 452
<212> TYPE: PRT
<213> ORGANISM: Homo sapiens
<220> FEATURE:
<223> OTHER INFORMATION: isocitrate dehydrogenase 2

<400> SEQUENCE: 2
```

-continued

```
Met Ala Gly Tyr Leu Arg Val Val Arg Ser Leu Cys Arg Ala Ser Gly
1               5                   10                  15

Ser Arg Pro Ala Trp Ala Pro Ala Ala Leu Thr Ala Pro Thr Ser Gln
            20                  25                  30

Glu Gln Pro Arg Arg His Tyr Ala Asp Lys Arg Ile Lys Val Ala Lys
        35                  40                  45

Pro Val Val Glu Met Asp Gly Asp Glu Met Thr Arg Ile Ile Trp Gln
50                  55                  60

Phe Ile Lys Glu Lys Leu Ile Leu Pro His Val Asp Ile Gln Leu Lys
65                  70                  75                  80

Tyr Phe Asp Leu Gly Leu Pro Asn Arg Asp Gln Thr Asp Asp Gln Val
                85                  90                  95

Thr Ile Asp Ser Ala Leu Ala Thr Gln Lys Tyr Ser Val Ala Val Lys
            100                 105                 110

Cys Ala Thr Ile Thr Pro Asp Glu Ala Arg Val Glu Glu Phe Lys Leu
        115                 120                 125

Lys Lys Met Trp Lys Ser Pro Asn Gly Thr Ile Arg Asn Ile Leu Gly
130                 135                 140

Gly Thr Val Phe Arg Glu Pro Ile Ile Cys Lys Asn Ile Pro Arg Leu
145                 150                 155                 160

Val Pro Gly Trp Thr Lys Pro Ile Thr Ile Gly Arg His Ala His Gly
                165                 170                 175

Asp Gln Tyr Lys Ala Thr Asp Phe Val Ala Asp Arg Ala Gly Thr Phe
            180                 185                 190

Lys Met Val Phe Thr Pro Lys Asp Gly Ser Gly Val Lys Glu Trp Glu
        195                 200                 205

Val Tyr Asn Phe Pro Ala Gly Gly Val Gly Met Gly Met Tyr Asn Thr
210                 215                 220

Asp Glu Ser Ile Ser Gly Phe Ala His Ser Cys Phe Gln Tyr Ala Ile
225                 230                 235                 240

Gln Lys Lys Trp Pro Leu Tyr Met Ser Thr Lys Asn Thr Ile Leu Lys
                245                 250                 255

Ala Tyr Asp Gly Arg Phe Lys Asp Ile Phe Gln Glu Ile Phe Asp Lys
            260                 265                 270

His Tyr Lys Thr Asp Phe Asp Lys Asn Lys Ile Trp Tyr Glu His Arg
        275                 280                 285

Leu Ile Asp Asp Met Val Ala Gln Val Leu Lys Ser Ser Gly Gly Phe
290                 295                 300

Val Trp Ala Cys Lys Asn Tyr Asp Gly Asp Val Gln Ser Asp Ile Leu
305                 310                 315                 320

Ala Gln Gly Phe Gly Ser Leu Gly Leu Met Thr Ser Val Leu Val Cys
                325                 330                 335

Pro Asp Gly Lys Thr Ile Glu Ala Glu Ala Ala His Gly Thr Val Thr
            340                 345                 350

Arg His Tyr Arg Glu His Gln Lys Gly Arg Pro Thr Ser Thr Asn Pro
        355                 360                 365

Ile Ala Ser Ile Phe Ala Trp Thr Arg Gly Leu Glu His Arg Gly Lys
370                 375                 380

Leu Asp Gly Asn Gln Asp Leu Ile Arg Phe Ala Gln Met Leu Glu Lys
385                 390                 395                 400

Val Cys Val Glu Thr Val Glu Ser Gly Ala Met Thr Lys Asp Leu Ala
                405                 410                 415
```

```
Gly Cys Ile His Gly Leu Ser Asn Val Lys Leu Asn Glu His Phe Leu
            420                 425                 430

Asn Thr Thr Asp Phe Leu Asp Thr Ile Lys Ser Asn Leu Asp Arg Ala
        435                 440                 445

Leu Gly Arg Gln
        450
```

MEANS AND METHODS FOR TREATING CANCER

This application is the U.S. National Stage of International Patent Application No. PCT/EP2014/059898, filed May 14, 2014, which claims the benefit of and priority to European Patent Application No. 14724722.5, filed May 14, 2013.

The present invention relates to a pharmaceutical composition comprising a compound of formula (I)

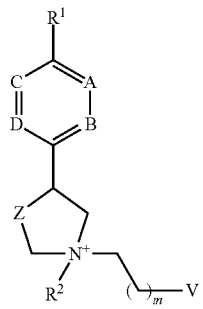

wherein $R^1$ is selected from halogen, substituted or unsubstituted $C_1$ to $C_6$ alkyl, substituted or unsubstituted $C_1$ to $C_6$ alkenyl, substituted or unsubstituted $C_1$ to $C_6$ alkynyl, substituted or unsubstituted $C_1$ to $C_6$ acyl, $C_1$ to $C_6$ haloalkyl, H, $NO_2$, OH, SH, $NH_2$, $C_1$ to $C_6$ alkoxy, CN and $N(CH_3)_2$, substituents being selected from OH, SH and $NH_2$, the term "substituted" providing for 1 or 2 substituents; $R^2$ is selected from H, substituted or unsubstituted $C_1$ to $C_6$ alkyl, substituted or unsubstituted $C_1$ to $C_6$ alkenyl and substituted or unsubstituted $C_1$ to $C_6$ alkynyl, substituents being selected from OH, SH and $NH_2$, the term "substituted" providing for 1 or 2 substituents; A, B, C and D are independently selected from N and CH; Z is selected from NH, S, $CH_2$, a direct single bond, and a direct double bond; V is selected from substituted or unsubstituted heterocycloalkyl, substituted or unsubstituted cycloalkyl, substituted or unsubstituted aryl, substituted or unsubstituted heteroaryl, heteroatoms in said heterocycloalkyl and said heteroaryl being selected from N, O and S, the total number of heteroatoms in said heterocycloalkyl and said heteroaryl being 1, 2, 3 or 4, the term "substituted" providing for 1, 2 or 3 substituents, substituents being selected from $C_1$ to $C_6$ alkyl, $C_1$ to $C_6$ alkenyl, $C_1$ to $C_6$ alkenyl, $C_1$ to $C_6$ acyl, $C_1$ to $C_6$ haloalkyl, $NO_2$, OH, SH, $NH_2$, $C_1$ to $C_6$ alkoxy, CN and $N(CH_3)_2$; and m is 0 or an integer selected from 1, 2, 3, 4 and 5.

In this specification, a number of documents including patent applications and manufacturer's manuals are cited. The disclosure of these documents, while not considered relevant for the patentability of this invention, is herewith incorporated by reference in its entirety. More specifically, all reference documents are incorporated by reference to the same extent as if each individual document was specifically and individually indicated to be incorporated by reference.

Isocitrate dehydrogenase, also known as IDH, is an enzyme which participates in the citric acid cycle. It catalyzes the third step of the cycle: the oxidative decarboxylation of isocitrate, producing alpha-ketoglutarate (α-ketoglutarate or α-KG) and $CO_2$ while converting NAD+ to NADH. This is a two-step process, which involves oxidation of isocitrate (a secondary alcohol) to oxalosuccinate (a ketone), followed by the decarboxylation of the carboxyl group beta to the ketone, forming alpha-ketoglutarate. Another isoform of the enzyme catalyzes the same reaction; however this reaction is unrelated to the citric acid cycle, is carried out in the cytosol as well as the mitochondrion and peroxisome, and uses NADP+ as a cofactor instead of NAD+.

Mutations in isocitrate dehydrogenase 1 (IDH1) and IDH2 were originally identified in glioma and acute myeloid leukemia (AML) patients (Mardis, E. R., Ding, L., Dooling, D. J., Larson, D. E. McLellan, M. D., Chen, K., Koboldt, D. C., Fulton, R. S., Delehaunty, K. D., McGrath, S. D., et al. (2009), Recurring mutations found by sequencing an acute myeloid leukemia genome. N Engl J Med 361, 1058-1066; Parsons, D. W., Jones, S., Zhang, X., Lin, J. C., Leary, R. J., Angenendt, P., Mankoo, P., Carter, H., Siu, I. M., Gallia, G. L., et al. (2008), An integrated genomic analysis of human glioblastoma multiforme. Science 321, 1807-1812; and Yan, H., Parsons, D. W., Jin, G., McLendon, R., Rasheed, B. A., Yuan, W., Kos, I., Batinic-Haberle, I., Jones, S., Riggins, G. J., et al. (2009), IDH1 and IDH2 mutations in gliomas. N Engl J Med 360, 765-773)), but are increasingly found in a diverse set of other tumor entities like chondrosarcoma (Amary, M. F., Bacsi, K., Maggiani, F., Damato, S., Halai, D., Berisha, F., Pollock, R., O'Donnell, P., Grigoriadis, A., Diss, T., et al. (2011), IDH1 and IDH2 mutations are frequent events in central chondrosarcoma and central and periosteal chondromas but not in other mesenchymal tumours. J Pathol 224, 334-343), lymphoma (Cairns, R. A., Iqbal, J., Lemonnier, F., Kucuk, C., de Leval, L., Jais, J. P., Parrens, M., Martin, A., Xerri, L., Brousset, P., et al. (2012), IDH2 mutations are frequent in angioimmunoblastic T-cell lymphoma. Blood 119, 1901-1903)), melanoma (Shibata, T., Kokubu, A., Miyamoto, M., Sasajima, Y., and Yamazaki, N. (2011), Mutant IDH1 confers an in vivo growth in a melanoma cell line with BRAF mutation. Am J Pathol 178, 1395-1402), and thyroid cancer (Murugan, A. K., Bojdani, E., and Xing, M. (2010), Identification and functional characterization of isocitrate dehydrogenase 1 (IDH1) mutations in thyroid cancer. Biochem Biophys Res Commun 393, 555-559). IDH mutations were identified in 15-30% of AML and other myeloid malignancies, including myelodysplastic syndromes (MDS) and myeloproliferative neoplasms (MPN) (Paschka, P., Schlenk, R. F., Gaidzik, V. I., Habdank, M., Kronke, J., Bulllinger, L., Spath, D., Kayser, S., Zucknick, M., Gotze, K., et al. (2010), IDH1 and IDH2 mutations are frequent genetic alterations in acute myeloid leukemia and confer adverse prognosis in cytogenetically normal acute myeloid leukemia with NPM1 mutation without FLT3 internal tandem duplication. J Clin Oncol 28, 3636-3643; Thol, F., Damm, F., Wagner, K., Gohring, G., Schlegelberger, B., Hoelzer, d., Lubbert, M., Heit, W., Kanz, L., Schlimok, G., et al. (2010), Prognostic impact of IDH2 mutations in cytogenetically normal acute myeloid leukemia, Blood 116, 614-616; and Wagner, K., Damm, F., Gohring, G., Gorlich, K., Heuser, M., Schafer, I., Ottmann, O., Lubbert, M., Heit, W., Kanz, L., et al. (2010), Impact of IDH1 R132 mutations and an IDH1 single nucleotide polymorphism in cytogenetically normal acute myeloid leukemia: SNP rs11554137 is an adverse prognostic factor. J Clin Oncol 28, 2356-2364). IDH mutations reside in the active site of the enzyme and participate in isocitrate binding. In many instances, they are missense alterations affecting arginine-140 (R140) residue in the IDH2 protein. IDH1 mutants lack the wild-type enzyme's ability to convert isocitrate to a α-ketoglutarate but gains a neomorphic activity which leads to the conversion of α-KG to the oncometabolite 2-hydroxyglutarate (2HG) (Dang, L., White, D. W., Gross, S., Bennett, B. D., Bittinger, M. A., Driggers, E. M., Fantin, V. R., Jang, H. G., Jin, S., Keenan, M. C., et al. (2009), Cancer-associated IDH1 mutations produce 2-hydroxyglutarate, Nature 462, 739-744; Gross, S., Cairns, R. A., Minden, M. D., Driggers, E. M., Bittinger, M. A., Jang, H. G., Sasaki, M., Jin, S., Schenkein, D. P., Su, S. M., et al. (2010), Cancer-associated metabolite 2-hydroxyglutarate accumulates in acute myelogenous leukemia with isocitrate dehydrogenase 1 and 2 mutations, J Exp Med 207, 339-344; and Ward, P. S., Cross, J. R., Lu, C., Weigert, O., Abel-Wahab, O., Levine, R. L., Weinstock, D. M., Sharp, K. A., and Thompson, C. B. (2012), Identification of additional IDH mutations associated with oncometabolite R(−)-2-hydroxyglutarate production. Oncogene 31, 2491-2498). It has been discovered that the product of neoactivity, 2HG, can be significantly elevated in cancer cells harbouring IDH1/2 mutations.

Given the disease relevance of isocitrate dehydrogenase, in particular mutated forms thereof, there is an unmet need of compounds targeting isocitrated dehydrogenase, preferably mutated forms thereof. Related thereto, there is an ongoing need for means and methods of treating cancer.

This technical problem is solved by the subject-matter of the enclosed claims.

Accordingly in the first aspect, the present invention relates to a pharmaceutical composition comprising a compound of formula (I)

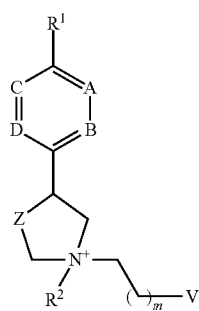

wherein $R^1$ is selected from halogen, substituted or unsubstituted $C_1$ to $C_6$ alkyl, substituted or unsubstituted $C_1$ to $C_6$ alkenyl, substituted or unsubstituted $C_1$ to $C_6$ alkenyl, substituted or unsubstituted $C_1$ to $C_6$ acyl, $C_1$ to $C_6$ haloalkyl, H, $NO_2$, OH, SH, $NH_2$, $C_1$ to $C_6$ alkoxy, CN and $N(CH_3)_2$, substituents being selected from OH, SH and $NH_2$, the term "substituted" providing for 1 or 2 substituents; $R^2$ is selected from H, substituted or unsubstituted $C_1$ to $C_6$ alkyl, substituted or unsubstituted $C_1$ to $C_6$ alkenyl and substituted or unsubstituted $C_1$ to $C_6$ alkynyl, substituents being selected from OH, SH and $NH_2$, substituents being selected from OH, SH and $NH_2$, the term "substituted" providing for 1 or 2 substituents; A, B, C and D are independently selected from N and CH; Z is selected from NH, S, $CH_2$, a direct single bond, and a direct double bond; V is selected from substituted or unsubstituted heterocycloalkyl, substituted or unsubstituted cycloalkyl, substituted or unsubstituted aryl, substituted or unsubstituted heteroaryl, heteroatoms in said heterocycloalkyl and said heteroaryl being selected from N, O and S, the total number of heteroatoms in said heterocycloalkyl and said heteroaryl being 1, 2, 3 or 4, the term "substituted" providing for 1, 2 or 3 substituents, substituents being selected from $C_1$ to $C_6$ alkyl, $C_1$ to $C_6$ alkenyl, $C_1$ to $C_6$ alkynyl, $C_1$ to $C_6$ acyl, $C_1$ to $C_6$ haloalkyl, $NO_2$, OH, SH, $NH_2$, $C_1$ to $C_6$ alkoxy, CN and $N(CH_3)_2$; and m is 0 or an integer selected from 1, 2, 3, 4 and 5.

It is noted that for each of moieties $R_1$, $R_2$ and V, the term "substituted" has a different meaning, which different meaning is clear from the wording of the embodiment of the first aspect. E.g., substituents selected from $C_1$ to $C_6$ alkyl, $C_1$ to $C_6$ alkenyl, $C_1$ to $C_6$ alkynyl, $C_1$ to $C_6$ acyl, $C_1$ to $C_6$ haloalkyl, $NO_2$, OH, SH, $NH_2$, $C_1$ to $C_6$ alkoxy, CN and $N(CH_3)_2$ are specific for substituted forms of moiety V such as substituted heterocycloalkyl.

The compounds according to the present invention, owing to the presence of a positive charge on the nitrogen atom depicted in formula (I), are to be provided with a counterion. Suitable counterions can be chosen by the skilled person without further ado. Preferred counterions include the halogenides, in particular Cl⁻ and Br⁻; as well as acetate and salicylate.

The skilled person can synthesize the compounds according to the present invention without further ado. The key step is the synthesis of 3-substituted pyrrolidine rings which can be performed as described, for example, in Laborde, Tetrahedron Lett. 33, 6607-6610 (1992) or Kurkin et al., Chem. Heterocycl. Comp. 43, 34-40 (2007). A corresponding general scheme is shown below.

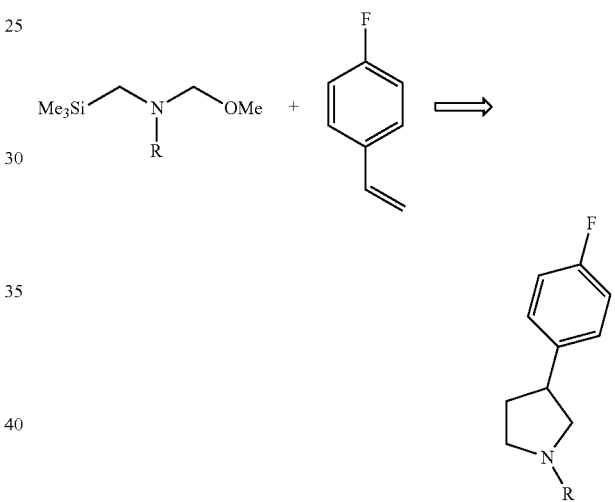

Moiety R in this scheme has its counterpart in the moiety comprising V and bound to N in formula (I).

Preferably, said haloalkyl is $CF_3$. Preferably, said alkoxy is $OCH_3$.

By virtue of their capability to bind and inhibit one or more mutant and/or wild-type isoforms of isocitrate dehydrogenase, the compounds according to the present invention are useful in the treatment of cancer, preferably those forms of cancer which are known to be isocitrate dehydrogenase-dependent.

The pharmaceutical composition may comprise or consist of one or more compounds in accordance with the present invention. In case it comprises one or more compounds according to the present invention, further constituents may be present. These further constituents may be pharmaceutically active compounds. Any further pharmaceutically active agents, to the extent they are present, may be selected from cancer, chemotherapeutic agents, antibodies directed against targets involved in cancer and hormones. Also, therapeutic treatment in accordance with the present invention may be combined with surgical treatment, in particular surgical removal of tumors. In other words, the subject or patient to be treated with the pharmaceutical composition of the invention may be a subject or patient who has undergone, is undergoing, or will undergo such surgical treatment.

Having said that, it is preferred that one or more compounds in accordance with the present invention are the only pharmaceutically active compound(s) comprised in said pharmaceutical composition.

To the extent said pharmaceutical composition comprises one or more compounds according to the present invention, it is furthermore envisaged that carriers, excipients and/or fillers as known in the pharmaceutical art are present.

The pharmaceutical composition will be formulated and dosed in a fashion consistent with good medical practice, taking into account the clinical condition of the individual patient, the site of delivery of the pharmaceutical composition, the method of administration, the scheduling of administration, and other factors known to practitioners. The effective amount of the pharmaceutical composition for purposes herein is thus determined by such considerations.

The skilled person knows that the effective amount of pharmaceutical composition administered to an individual will, inter alia, depend on the nature of the compound. For example, the total pharmaceutically effective amount of pharmaceutical composition administered parenterally or orally per dose may be in the range of about 1 µg compound/kg/day to 50 mg compound/kg/day of patient body weight, although, as noted above, this will be subject to therapeutic discretion. More preferably, this dose is at least 0.01 mg compound/kg/day, and most preferably for humans between about 0.01 and about 50 mg compound/kg/day. If given continuously, the pharmaceutical composition is typically administered at a dose rate of about 1 µg/kg/hour to about 500 µg/kg/hour, either by 1-4 injections per day or by continuous subcutaneous infusions, for example, using a mini-pump. An intravenous bag solution may also be employed. Alternatively, the compound may be administered orally in one or up to 5 doses per day at a dose range of about 1 µg compound/kg/day to about 50 mg compound/kg/day of patient body weight. The length of treatment needed to observe changes and the interval following treatment for responses to occur appears to vary depending on the desired effect. The particular amounts may be determined by conventional tests which are well known to the person skilled in the art.

Pharmaceutical compositions of the invention may be administered orally, rectally, parenterally including intravenously, intrathecally, intracisternally, intravaginally, intraperitoneally, topically (as by powders, ointments, drops or transdermal patch), bucally, or as an oral or nasal spray.

Pharmaceutical compositions of the invention preferably comprise a pharmaceutically acceptable carrier. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The pharmaceutical composition is also suitably administered by sustained release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(-)-3-hydroxybutyric acid (EP 133,988). Sustained release pharmaceutical composition also include liposomally entrapped compound. Liposomes containing the pharmaceutical composition are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy.

For parenteral administration, the pharmaceutical composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the components of the pharmaceutical composition uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The components of the pharmaceutical composition to be used for therapeutic administration must be sterile. Sterility is readily accomplished by filtration through sterile filtration membranes (e.g., 0.2 micron membranes). Therapeutic components of the pharmaceutical composition generally are placed into a container having a sterile access port, for example, an intravenous solution bag or vial having a stopper pierceable by a hypodermic injection needle.

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The solution for infusion or injection is prepared by reconstituting the lyophilized compound(s) using bacteriostatic Water-for-Injection. The compounds described herein can, for example, be administered per orally, by injection, intravenously, intraarterially, subdermally, intraperitoneally, intramuscularly, or subcutaneously.

Generally speaking, as regards the number of carbon atoms in any moiety defined to be $C_1$ to $C_6$, it is preferred that the moiety contains between 1 and 4 carbon atoms. Particularly preferred is $C_1$ and $C_2$.

In a preferred embodiment, A, B, C and D are CH. Also preferred is that either A or B is N, the remainder of A, B, C and D being CH.

In a further preferred embodiment, Z is $CH_2$ or NH. Particularly preferred is that Z is $CH_2$.

In a further preferred embodiment, m is 0, 1 or 2, preferably 1.

In a further preferred embodiment, V is substituted or unsubstituted heterocycloalkyl, preferably substituted or unsubstituted piperazinyl, more preferably substituted or unsubstituted piperazin-2-yl, and yet more preferably 1,4-dimethyl-piperazin-2-yl.

In other words, preferred pharmaceutical compositions are those comprising a compound of formula (Ia)

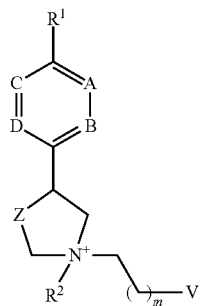

wherein $R^1$ is selected from halogen, substituted or unsubstituted $C_1$ to $C_6$ alkyl, substituted or unsubstituted $C_1$ to $C_6$ alkenyl, substituted or unsubstituted $C_1$ to $C_6$ alkynyl, substituted or unsubstituted $C_1$ to $C_6$ acyl, $C_1$ to $C_6$ haloalkyl, H, $NO_2$, OH, SH, $NH_2$, $C_1$ to $C_6$ alkoxy, CN and $N(CH_3)_2$, substituents being selected from OH, SH and $NH_2$, the term "substituted" providing for 1 or 2 substituents; $R^2$ is selected from H, substituted or unsubstituted $C_1$ to $C_6$ alkyl, substituted or unsubstituted $C_1$ to $C_6$ alkenyl and substituted or unsubstituted $C_1$ to $C_6$ alkynyl, substituents being selected from OH, SH and $NH_2$, substituents being selected from OH, SH and $NH_2$, the term "substituted" providing for 1 or 2 substituents; A, B, C and D are independently selected from N and CH; Z is selected from NH, S, $CH_2$, a direct single bond, and a direct double bond; V is selected from substituted or unsubstituted heterocycloalkyl, heteroatoms in said heterocycloalkyl being selected from N, O and S, the total number of heteroatoms in said heterocycloalkyl being 1, 2, 3 or 4, the term "substituted" providing for 1, 2 or 3 substituents, substituents being selected from $C_1$ to $C_6$ alkyl, $C_1$ to $C_6$ alkenyl, $C_1$ to $C_6$ alkynyl, $C_1$ to $C_6$ acyl, $C_1$ to $C_6$ haloalkyl, $NO_2$, OH, SH, $NH_2$, $C_1$ to $C_6$ alkoxy, CN and $N(CH_3)_2$; and m is 0 or an integer selected from 1, 2, 3, 4 and 5.

A particularly preferred class of compounds in accordance with the present invention are the compounds of formula (V)

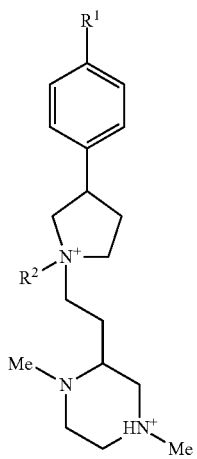

$R^1$ and $R^2$ are as defined in accordance with the first aspect or preferably in accordance with the preferred embodiments described below.

In a further preferred embodiment, $R^1$ is halogen, preferably F, Cl or Br

In a further preferred embodiment, $R^2$ is H.

In a further preferred embodiment of the first aspect of the invention or any of its above described preferred embodiments, the stereochemistry of said compound is as shown in formula (II)

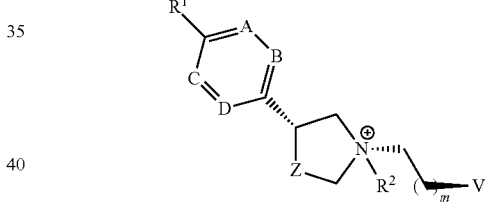

In particularly preferred embodiments of the pharmaceutical composition of the present invention, said compound is a compound of formula (III)

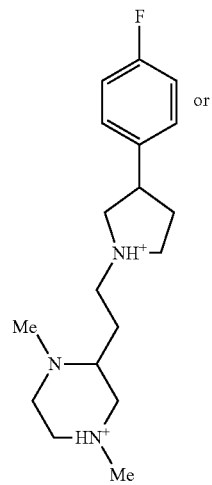

-continued

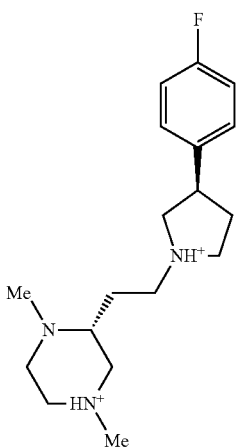

(IV)

This compound is also referred to as HMS-101 herein.

The compound of this invention may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Preferably, the compounds according to the present invention are furthermore characterized, more preferably inherently characterized, by the following features. In particular, it is preferred said compound (a) inhibits a mutant form of at least one isoform of isocitrate dehydrogenase, said mutant preferably being characterized by one or more of the following: (i) reduced formation of α-ketoglutarate by the encoded isocitrate dehydrogenase as compared to the wild-type isocitrate dehydrogenase; (ii) increased formation of 2-hydroxyglutarate by the encoded isocitrate dehydrogenase as compared to the wild-type isocitrate dehydrogenase; (iii) no increased formation of 2-hydroxyglutarate by the encoded isocitrate dehydrogenase as compared to the wild-type isocitrate dehydrogenase; (iv) aberrant splicing such as absence of exon 7 in the spliced mRNA; (v) a missense mutation affecting R132 in human isocitrate dehydrogenase 1; (vi) a missense mutation affecting R172 in human isocitrate dehydrogenase 2; (vii) a missense mutation affecting R140 in human isocitrate dehydrogenase 2; (viii) a missense mutation affecting R100 in human isocitrate dehydrogenase 1; and (ix) a missense mutation affecting G97 in human isocitrate dehydrogenase 1; and/or (b) binds to a pocket in the three-dimensional structure of said mutant form of at least one isoform of isocitrate dehydrogenase, said pocket being absent in the corresponding wild-type form(s).

The term "isoform of isocitrate dehydrogenase" includes isocitrate dehydrogenase 1 and isocitrate dehydrogenase 2. The sequences of human isocitrate dehydrogenase 1 and human isocitrate dehydrogenase 2 are herewith included as SEQ ID NOs: 1 and 2.

The specific mutations according to items (v) to (ix) are preferred mutations which lead to the increased formation of 2-hydroxyglutarate. Preferred missense mutations affecting R132 in accordance with above item (v) are R132H (also referred to as IDHmut herein) as well as R132C. In particular these two mutants have been further investigated in the Examples enclosed herewith.

It is understood that item (a) provides for the presence of one or more of features (i) to (ix). To give an example, aberrant splicing in accordance with (a)(iv) may be observed in a mutant form of isocitrate dehydrogenase which differs from the corresponding wild-type only in that said aberrant splicing occurs, or, in the alternative, aberrant splicing may affect a mutant of isocitrate dehydrogenase in which case there would be concomitant presence of aberrant splicing and a further mutation, said further mutation not necessarily being related to the process of splicing.

As regards sub-items (ii) and (iii), we note that preference is given to those mutants which are characterized by the increased formation of 2-hydroxyglutarate, in particular of R-2-hydroxyglutarate (also known as D-2-hydroxyglutarate). As noted above, 2-hydroxyglutarate is being viewed as a oncometabolite and accordingly as a hallmark of IDH mutant-associated cancer. More specifically, and as noted above, it is R-2-hydroxyglutarate which is a marker for IDH mutant-associated cancer, in particular leukemia. Elevated levels of R-2-hydroxyglutarate may be measured in terms of the ratio R-2-hydroxyglutarate/S-2-hydroxyglutarate. Exemplary data can be found in FIGS. 2 and 6 enclosed herewith.

Yet, the present inventors surprisingly observed that mutated isocitrate dehydrogenase, in particular an alternatively spliced isoform of mutated IDH1, may promote leukemogenesis independently of 2-hydroxyglutarate. As a consequence, it is preferred that compounds according to the present invention also target mutant forms of isocitrate dehydrogenase which are not characterized by increased formation of 2-hydroxyglutarate.

Furthermore, the inventors surprisingly observed that compounds in accordance with the present invention were effective also in certain leukemia patients which have wild-type isocitrate dehydrogenase. As a consequence, while isocitrate dehydrogenase is still viewed to be a key molecule for the neoplasia seen in these patients, it is important to note that also targeting the wild-type form of isocitrate dehydrogenase may be beneficial. This applies in particular, but not only, to individuals or patients with increased expression and/or activity of at least one isoform of isocitrate dehydrogenase.

The term "increased expression" refers to an expression at the mRNA or protein level which is elevated as compared to the average expression at the mRNA or protein level, respectively, in healthy individuals. Similarly, the term "increased activity" refers to increased activity as compared to the average activity in healthy individuals. The term "activity" preferably is the enzymatic activity, in particular the formation of alpha-ketoglutarate or 2-hydroxyglutarate. The term "increased" refers in this context to an increase of 200, 300, 400, 500, 600, 700, 800, 900 or 1000% or more percent. Also envisaged is a twofold, threefold, fourfold, fivefold to tenfold or higher increase of expression or activity.

In a preferred embodiment, said compound binds to and/or inhibits said mutant form to a higher degree than (to) the corresponding wild-type form.

As stated above, such type of specificity is generally preferred. On the other hand, it is not a strict necessity, noting that also patients having cancer and a wild-type isocitrate dehydrogenase benefit from treatment with compounds in accordance with the present invention.

In view of the documented relevance of isocitrate dehydrogenase for cancer in general and various specific forms thereof, the present invention provides in a second aspect a compound as defined above for use in a method of treating or preventing a cell proliferation disorder, said disorder preferably being a hyperplasia, tumor or cancer, more preferably being selected from leukemia including myeloid leukemia such as acute myeloid leukemia (AML), myeloid malignancies including myelodysplastic syndrome (MDS) and myeloproliferative neoplasms (MPN), glioma, lymphoma, and solid tumors including prostate cancer, thyroid cancer, sarcomas such as fibrosarcoma and chondrosarcoma, and melanoma.

In a preferred embodiment, the subject suffering from or being at risk of said disorder is (a) characterized by increased expression and/or activity of at least one isoform of isocitrate dehydrogenase; or (b) heterozygous or homozygous with regard to a mutant form of at least one isoform of isocitrate dehydrogenase, said mutant preferably being characterized by one or more of the following: (i) reduced formation of α-ketoglutarate by the encoded isocitrate dehydrogenase as compared to the wild-type isocitrate dehydrogenase; (ii) increased formation of 2-hydroxyglutarate by the encoded isocitrate dehydrogenase as compared to the wild-type isocitrate dehydrogenase; (iii) no increased formation of 2-hydroxyglutarate by the encoded isocitrate dehydrogenase as compared to the wild-type isocitrate dehydrogenase; (iv) aberrant splicing such as absence of exon 7 in the spliced mRNA; (v) a missense mutation affecting R132 in human isocitrate dehydrogenase 1; (vi) a missense mutation affecting R172 in human isocitrate dehydrogenase 2; (vii) a missense mutation affecting R140 in human isocitrate dehydrogenase 2; (viii) a missense mutation affecting R100 in human isocitrate dehydrogenase 1; and (ix) a missense mutation affecting G97 in human isocitrate dehydrogenase 1.

In a third aspect, the present invention provides a method of treating or preventing a cell proliferation disorder, said disorder preferably being a hyperplasia, tumor or cancer, more preferably being selected from leukemia including myeloid leukemia such as acute myeloid leukemia (AML), myeloid malignancies including myelodysplastic syndrome (MDS) and myeloproliferative neoplasms (MPN), glioma, lymphoma, and solid tumors including prostate cancer, thyroid cancer, sarcomas such as fibrosarcoma and chondrosarcoma, and melanoma, said method comprising the step of administering a therapeutically active amount or a preventive amount of a compound as defined above.

In a further aspect, the present invention provides a mouse being characterized by (a) an activated gene of the HOXA cluster, preferably HOXA 9; and (b) (ba) increased expression and/or activity of at least one isoform of isocitrate dehydrogenase; or (bb) presence of a mutant form of at least one isoform of isocitrate dehydrogenase, said mutant preferably being characterized by one or more of the following: (i) reduced formation of α-ketoglutarate by the encoded isocitrate dehydrogenase as compared to the wild-type isocitrate dehydrogenase; (ii) increased formation of 2-hydroxyglutarate by the encoded isocitrate dehydrogenase as compared to the wild-type isocitrate dehydrogenase; (iii) no increased formation of 2-hydroxyglutarate by the encoded isocitrate dehydrogenase as compared to the wild-type isocitrate dehydrogenase; (iv) aberrant splicing such as absence of exon 7 in the spliced mRNA; (v) a missense mutation affecting R132 in human isocitrate dehydrogenase 1; (vi) a missense mutation affecting R172 in human isocitrate dehydrogenase 2; (vii) a missense mutation affecting R140 in human isocitrate dehydrogenase 2; (viii) a missense mutation affecting R100 in human isocitrate dehydrogenase 1; and (ix) a missense mutation affecting G97 in human isocitrate dehydrogenase 1.

Preferred means of activating a gene of the HOXA cluster, preferably HOXA 9, are retroviral overexpression, lentiviral overexpression, or overexpression in a transgenic model. It is understood that overexpression is a preferred implementation of activation. Both activation and overexpression are defined by reference to the parent strain from which the mouse according to the present invention has been derived from. A preferred parent strain is strain C57BL6. Preferred is an increase in expression as compared to the parent strain of at least 10%, at least 20%, at least 30%, at least 40%, at least 50% or more. Also envisaged is twofold, threefold, fourfold, fivefold, tenfold or higher overexpression.

The above defined mouse model is a preferred model for in vivo screens directed to the identification and/or validation of compounds targeting isocitrate dehydrogenase in a disease-relevant context. More specifically, said mouse model recapitulates leukemogenesis. The present inventors used said mouse model in order to establish that production of 2-hydroxyglutarate, while being a preferred feature characterizing aberrantly proliferating cells with mutated isocitrate dehydrogenase, is not a requirement for oncogenic activity of mutated isocitrate dehydrogenase.

The figures show:

FIG. 1: IC50 values for IDH1wt and IDH1mut treated with compound HMS-101 for 72 hours. The compound described herein has an IC50 of 1 μM on IDH1mut cancer cells in vitro, whereas it has a 12 times higher IC50 (12 μM) on IDH1wt cells in vitro as analysed by Alamar blue cell viability assay.

Figure 2:
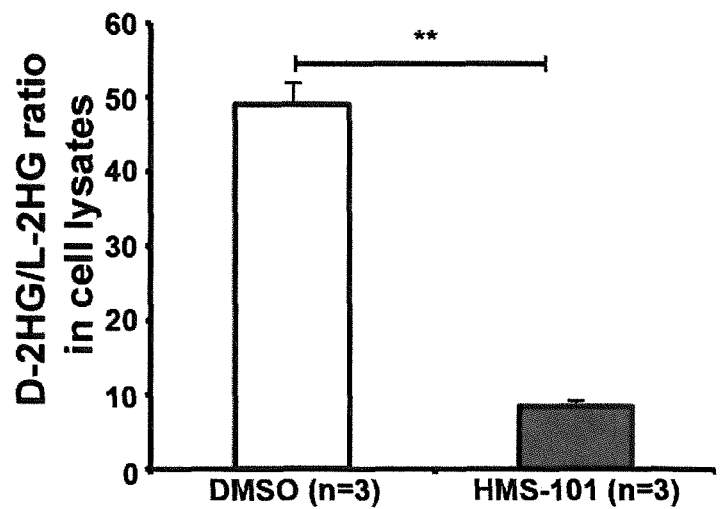

FIG. 2: D-2HG levels from IDH1mut cells treated with compound HMS-101 (drug) or solvent control. The compound described herein has reduced the neomorphic activity of the IDH1mutant enzyme, i.e. the production of 2HG, as evident by dramatically reduced intracellular 2HG levels in IDH1mutant cells treated with compound HMS-101 for 72 hours at 10 μM dose of compound as compared to the control treated cells.

Figure 3:
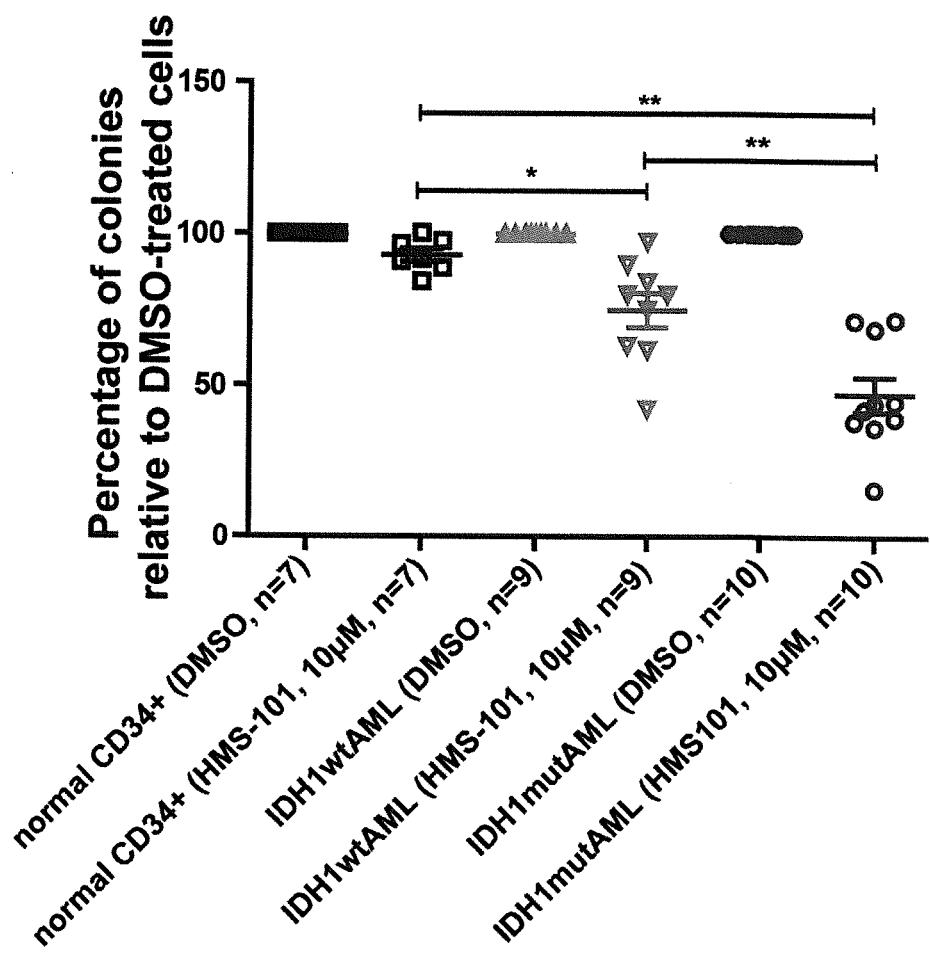

FIG. 3: Colony forming assay of primary human AML cells with and without IDH1 mutation treated with solvent control (DMSO) or compound HMS-101. Human CD34+ hematopoietic stem and progenitor cells from healthy donors were used as controls. The compound HMS-101 reduced the colony forming potential of primary human AML cells harboring the IDH1 mutation when compared to primary human AML cells with wildtype IDH1 and cells from healthy donors.

Figure 4:
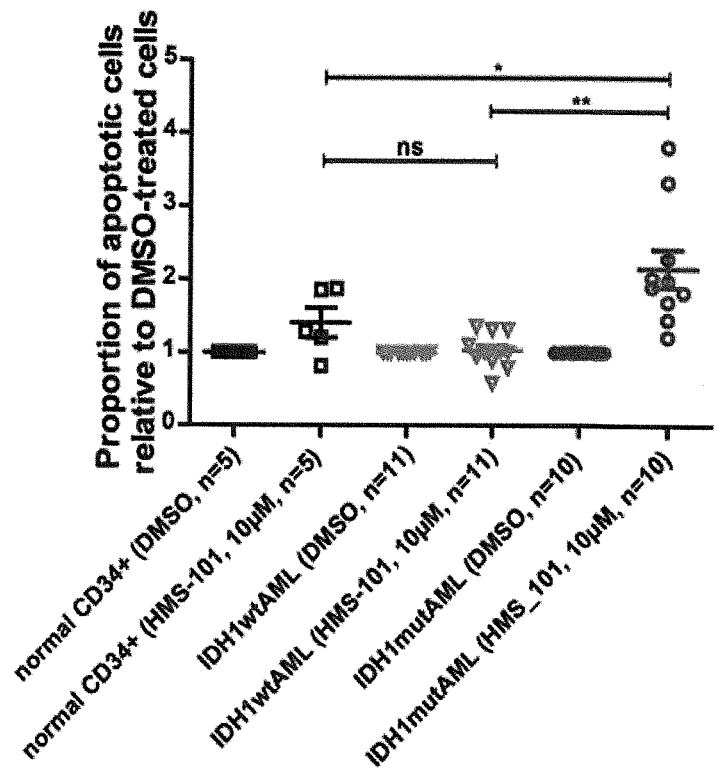

FIG. 4: Rate of apoptosis of primary human AML cells with and without IDH1 mutation treated with solvent control (DMSO) or compound HMS-101. Human CD34+ hematopoietic stem and progenitor cells from healthy donors were used as controls. The compound HMS-101 increased the rate of apoptosis of primary human AML cells harboring the IDH1 mutation significantly more compared to primary human AML cells with wildtype IDH1 and cells from healthy donors.

Figure 5:
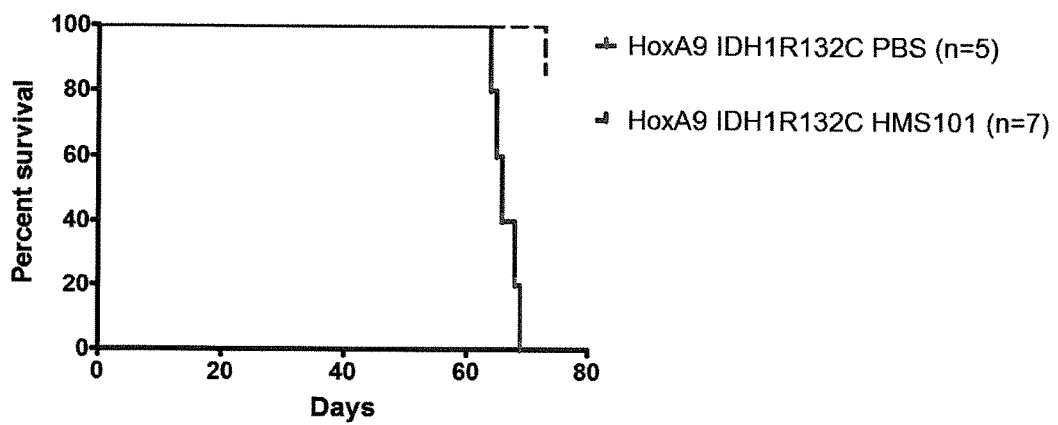

FIG. 5: Survival of mice treated with HMS-101.

Figure 6:
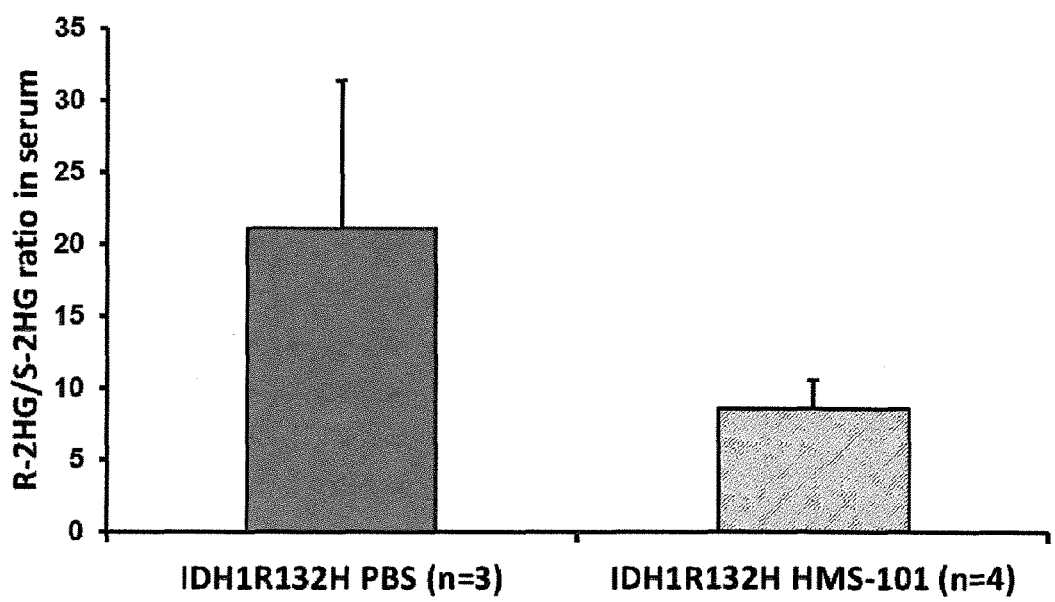

FIG. 6: Ratio of R-2-hydroxyglutarate (R-2HG) to S-2-hydroxyglutarate (S-2HG) in serum from mice treated with HMS-101 or solvent control (PBS) at 9 weeks after treatment. Serum from 3 mice were pooled per indicated measurement (9 mice for PBS, 12 mice for HMS-101).

The following examples illustrate the invention.

EXAMPLE 1

Affinity of Compound with IDH Mutant

The predicted affinity (in silico modeling) of compound HMS-101 to IDH1 is comparable to IDH inhibitor compounds published recently[15] (ΔG≈8 kcal/mol). The compound HMS-101 has significantly better predicted affinity (ΔΔG≈10 kcal/mol) for IDHmut (R132H) in the presence of NADP than to wildtype IDH1. In the absence of NADP, the compound described herein has selectivity towards mutant but not as pronounced as with presence of NADP. This high selectivity is favorable compared to compounds recently patented[16], which show selectivity to the IDH1 mutant by ΔΔG≈1-2 kcal/mol.

EXAMPLE 2

Toxicity Testing in Animals

The compound described herein has been given to mice at a dose of 1 mg intraperitoneally daily for two weeks. The compound was well tolerated by the animals with no visible signs of toxicity.

EXAMPLE 3

In Vitro Proliferation of Cancer Cells (IC50)

The compound described herein has an IC50 of 1 μM on IDH1mut cancer cells in vitro, whereas it has a 12 times higher IC50 (12 μM) on IDH1 wt cells in vitro as analysed by Alamar blue cell viability assay (FIG. 1).

EXAMPLE 4

Neoactivity of IDHmut Enzyme

The compound described herein has reduced the neomorphic activity of the IDH1 mutant enzyme, i.e. the production of 2HG, as evident by dramatically reduced intracellular 2HG levels in IDH1mutant cells treated with compound HMS-101 for 72 hours at 10 μM dose of compound as compared to the control treated cells (FIG. 2).

EXAMPLE 5

Effect of Compound HMS-101 on the Colony Forming Potential of Primary Human Acute Myeloid Leukemia Cells The compound HMS-101 reduced the colony forming potential of primary human AML cells harboring the IDH1 mutation when compared to primary human AML cells with wildtype IDH1 and cells from healthy donors (FIG. 3).

EXAMPLE 6

Effect of Compound HMS-101 on the Rate of Apoptosis of Primary Human AML Cells

The compound HMS-101 increased the rate of apoptosis of primary human AML cells harboring the IDH1 mutation significantly more compared to primary human AML cells with wildtype IDH1 and cells from healthy donors (FIG. 4).

EXAMPLE 7

In Vivo Effect of HMS-101

HoxA9 immortalized bone marrow cells from C57BL/6J mice were transduced with retroviral vectors expressing IDH1R132C and GFP. One million GFP-expressing sorted cells were injected intravenously in lethally-irradiated syngeneic recipient mice, accompanied by a life-sparing dose of $1 \times 10^5$ freshly isolated bone marrow cells from syngeneic mice. One cohort of mice was treated with HMS-101 at a dose of 1 mg/mouse for 5 days/week starting 5 days after transplantation. The control cohort was treated with PBS for 5 days/week starting 5 days after transplantation. The solid line represents the survival of PBS-treated mice, the dotted line represents the survival of HMS-101-treated mice. Follow-up and treatment are ongoing. As all control mice are dead, the graph indicates a survival benefit for HMS-101 treated mice.

EXAMPLE 8

2-Hydroxyglutarate as Marker for Leukemia 2-hydroxyglutarate (R-2HG), in particular elevated values thereof, typically measured in terms of the ratio between R- and S-form (R-2HG/S-2HG) is a marker for leukemia in accordance with the present invention. As shown in FIG. 6, treatment with a preferred compound in accordance with the present invention (HMS-101) causes a decrease of the ratio R-2HG/S-2HG in treated mice. This establishes both the usefulness of the mentioned ratio as a marker for leukemia and the beneficial effects of HMS-101.

The invention claimed is:

1. A method of treating or preventing a cell proliferation disorder, said method comprising the step of treating a subject suffering from or being at risk of the cell proliferation disorder with a therapeutically active amount or a preventive amount of a compound formula (I):

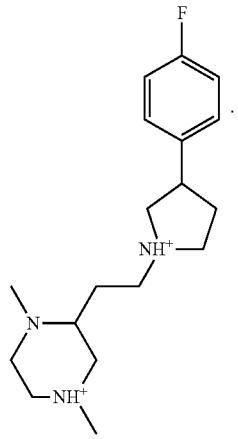 [SMILES: CN1CC[NH+](C)CC1CC[NH+]1CCC(c2ccc(F)cc2)C1]

2. The method of claim 1, wherein the cell proliferation disorder is leukemia, glioma, lymphoma, prostate cancer, thyroid cancer, or sarcoma.

3. The method of claim 2, wherein the subject suffering from or being at risk of said disorder is
   (a) characterized by increased expression and/or activity of at least one isoform of isocitrate dehydrogenase; or
   (b) heterozygous or homozygous with regard to a mutant form of at least one isoform of isocitrate dehydrogenase.

4. The method of claim 1, wherein the subject suffering from or being at risk of said disorder is heterozygous or homozygous with regard to a mutant form of at least one isoform of isocitrate dehydrogenase and further wherein said mutant form is characterized by one or more of the following:

(i) reduced formation of α-ketoglutarate by the encoded isocitrate dehydrogenase as compared to the wild-type isocitrate dehydrogenase;
   (ii) increased formation of 2-hydroxyglutarate by the encoded isocitrate dehydrogenase as compared to the wild-type isocitrate dehydrogenase;
   (iii) no increased formation of 2-hydroxyglutarate by the encoded isocitrate dehydrogenase as compared to the wild-type isocitrate dehydrogenase;
   (iv) aberrant splicing such as absence of exon 7 in the spliced mRNA;
   (v) a missense mutation affecting R132 in human isocitrate dehydrogenase 1;
   (vi) a missense mutation affecting R172 in human isocitrate dehydrogenase 2;
   (vii) a missense mutation affecting R140 in human isocitrate dehydrogenase 2;
   (viii) a missense mutation affecting R100 in human isocitrate dehydrogenase 1; and
   (ix) a missense mutation affecting G97 in human isocitrate dehydrogenase 1.

5. The method of claim 1, wherein the compound is of formula (IV)

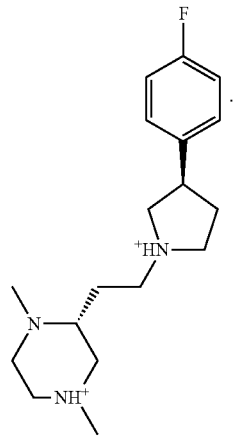 [SMILES: CN1CC[NH+](C)C[C@H]1CC[NH+]1CC[C@H](c2ccc(F)cc2)C1]

* * * * *